(12) United States Patent
Matheny

(10) Patent No.: US 9,433,491 B1
(45) Date of Patent: Sep. 6, 2016

(54) TISSUE PROSTHESES FOR REPAIRING, RECONSTRUCTING AND REPLACING DAMAGED OR DISEASED BIOLOGICAL STRUCTURES AND ASSOCIATED TISSUE

(71) Applicant: CorMatrix Cardiovascular, Inc., Roswell, GA (US)

(72) Inventor: Robert G Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 0 days.

(21) Appl. No.: 15/144,902

(22) Filed: May 3, 2016

Related U.S. Application Data

(60) Division of application No. 14/635,118, filed on Mar. 2, 2015, now Pat. No. 9,352,070, and a continuation-in-part of application No. 14/337,863, filed on Jul. 22, 2014, now abandoned.

(51) Int. Cl.
| | |
|---|---|
| *A61F 2/04* | (2013.01) |
| *A61L 27/36* | (2006.01) |
| *A61L 27/34* | (2006.01) |
| *A61F 2/06* | (2013.01) |
| *A61L 27/54* | (2006.01) |

(52) U.S. Cl.
CPC . *A61F 2/04* (2013.01); *A61F 2/06* (2013.01); *A61L 27/34* (2013.01); *A61L 27/36* (2013.01); *A61L 27/3625* (2013.01); *A61L 27/3629* (2013.01); *A61L 27/3633* (2013.01); *A61L 27/54* (2013.01); *A61F 2002/041* (2013.01); *A61F 2002/043* (2013.01); *A61F 2002/044* (2013.01); *A61F 2002/045* (2013.01); *A61F 2002/046* (2013.01); *A61F 2002/047* (2013.01); *A61F 2002/048* (2013.01); *A61L 2300/40* (2013.01); *A61L 2300/414* (2013.01)

(58) Field of Classification Search
CPC ...... A61F 2/04; A61F 2/06; A61F 2002/041; A61F 2002/046; A61F 2002/047; A61F 2002/045; A61F 2002/048; A61F 2002/044; A61L 27/36; A61L 27/34; A61L 27/3625; A61L 27/54; A61L 27/3629; A61L 27/3633; A61L 2300/414; A61L 2300/40
See application file for complete search history.

(56) References Cited

FOREIGN PATENT DOCUMENTS

| WO | WO 2013/154612 A2 * | 10/2013 | ............ A61L 27/56 |
| WO | WO 2014/044321 A1 * | 3/2014 | ............ A61L 27/26 |

OTHER PUBLICATIONS

Chen et al. (Biomaterials 31 (2010) 3885-3893).*
Ravi et al. (Regen Med. Jan. 2010; 5(1): pp. 1-21).*
Sant et al. (Aug. 2010, "Fabrication and characterization of tough elastomeric fibrous scaffolds for tissue engineering applications," Engineering in Medicine and Biology Society (EMBC), 2010 Annual International Conference of the IEEE, pp. 3546-3548).*

* cited by examiner

*Primary Examiner* — Aradhana Sasan
(74) *Attorney, Agent, or Firm* — Francis Law Group

(57) ABSTRACT

Non-antigenic, bioremodelable tissue prostheses that can be engineered into a variety of shapes and used to repair, augment, reconstruct or replace damaged or diseased biological structures and associated tissue.

9 Claims, 2 Drawing Sheets

TISSUE PROSTHESES FOR REPAIRING, RECONSTRUCTING AND REPLACING DAMAGED OR DISEASED BIOLOGICAL STRUCTURES AND ASSOCIATED TISSUE

CROSS-REFERENCES TO RELATED APPLICATIONS

This application is a division of U.S. application Ser. No. 14/635,118, filed on Mar. 2, 2015, which is a continuation-in-part of U.S. application Ser. No. 14/337,863, filed on Jul. 22, 2014.

FIELD OF THE INVENTION

The present invention relates to methods and apparatus for reconstructing or replacing damaged or diseased cardiovascular vessels. More particularly, the present invention relates to tissue prostheses in the form of seamless tubular members or grafts for repairing, augmenting, reconstructing or replacing damaged or diseased biological structures and associated tissue.

BACKGROUND OF THE INVENTION

As is well known in the art, various prostheses are often employed to reconstruct or replace damaged or diseased cardiovascular vessels.

Currently, the prostheses often employed to reconstruct or replace damaged or diseased cardiovascular vessels are autologous arteries and veins, e.g., internal mammary artery or saphenous vein; particularly, in situations where small diameter (i.e. 3-4 mm) vessels are required, such as below the knee and coronary artery bypass grafting.

Autologous arteries and veins are, however, often unavailable, due to prior harvest, or unsuitable, due to arterial disease.

When autologous arteries and veins are unavailable or unsuitable, synthetic polytatrafluoroethylene (PTFE) or Dacron® grafts are often employed to reconstruct or replace damaged or diseased cardiovascular vessels; particularly, in situations where large diameter (i.e. ≥6 mm) vessels are required.

There are, however, numerous drawbacks and disadvantages associated with synthetic prostheses. A major drawback is the poor median patency exhibited by synthetic prostheses, due to stenosis, thromboembolization, calcium deposition and infection. Indeed, it has been found that patency is >25% @ 3 years using synthetic and cryopreserved prostheses in peripheral and coronary bypass surgeries, compared to >70% for autologous vascular conduits. See Chard, et al., *Aorta-Coronary Bypass Grafting with Polytetrafluoroehtylene Conduits: Early and Late Outcome in Eight Patients*, j Thorac Cardiovasc Surg, vol. 94, pp. 312-134 (1987).

Decellularized bovine internal jugular xenografts and human allograft vessels from cadavers have also employed to reconstruct or replace damaged or diseased cardiovascular vessels. Such materials and structures are, however, prone to calcification and thrombosis and, thus, have not gained significant clinical acceptance.

Vascular prostheses constructed of various biodegradable materials, such as poly (trimethylene carbonate), have also been developed to reconstruct or replace damaged or diseased cardiovascular vessels. There are, however, several drawbacks and disadvantages associated with such prostheses.

One major disadvantage is that the biodegradable materials and, hence, prostheses formed therefrom, often break down at a faster rate than is desirable for the application. A further disadvantage is that the materials can, and in many instances will, break down into large, rigid fragments that can cause obstructions in the interior of the vessel and cause inflammation.

More recently, prostheses comprising various remodelable materials, such as extracellular matrix (ECM®) sheets, have been developed to reconstruct or replace damaged or diseased cardiovascular vessels. Illustrative are the ECM® prostheses disclosed in Applicant's Co-Pending application Ser. No. 13/573,226.

Although such materials and prostheses formed therewith have garnered overwhelming success and, henc$^e$, gained significant clinical acceptance, there are a few drawbacks associated with such grafts. Among the drawbacks are the construction and, hence, configuration of the noted prostheses.

As discussed in detail in Co-Pending application Ser. No. 13/573,226, such prostheses typically comprise one or more sheets of ECM tissue, e.g., small intestine submucosa, which is secured at one edge to form a tubular structure. The secured edge or seam can, and in many instances will, disrupt blood flow through the graft. A poorly secured edge also poses a significant risk of thrombosis and cause turbulent flow.

Further, in some instances, wherein the ECM prostheses comprise two or more sheets, i.e. a multi-sheet laminate, the laminate structure may delaminate.

Thus, readily available, versatile tissue prostheses that are not prone to calcification, thrombosis and intimal hyperplasia would fill a substantial and growing clinical need.

It is therefore an object of the present invention to provide tissue prostheses in the form of seamless tubular members (or structures) or graft structures that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

It is another object of the present invention to provide tissue prostheses that can effectively replace or improve biological functions or promote the growth of new tissue in a subject.

It is another object of the present invention to provide tissue prostheses that induce "modulated healing" of damaged biological structures and/or damaged tissue associated therewith, including modulation of inflammation, and host tissue proliferation, bioremodeling and regeneration of new tissue and tissue structures with site-specific structural and functional properties.

It is another object of the present invention to provide tissue prostheses that are capable of administering a biologically active and/or pharmacological agent to host tissue and, thereby, produce a desired biological and/or therapeutic effect.

SUMMARY OF THE INVENTION

The present invention is directed to non-antigenic, resilient, bioremodelable, biocompatible tissue prostheses that can be engineered into a variety of shapes and used to repair, augment, reconstruct or replace damaged or diseased biological structures and associated tissue, including a pericardium, myocardium, heart valve, an aorta, artery, vein and vena cava, and other biological structures, including, without limitation, an esophagus, trachea, bronchus, ureter, urethra, bile duct, and small and large intestine. The tissue prostheses can also be readily employed to reconstruct or replace damaged or diseased dura around a spinal cord.

In a preferred embodiment of the invention, the tissue prostheses comprise seamless tubular members or conduits and graft structures.

As discussed in detail herein, in a preferred embodiment, the seamless tubular members (or conduits) comprise seamless tubular structures having first (or proximal) and second (or distal) ends.

According to the invention, the seamless tubular structures can comprise any mammalian tubular structure, including, without limitation, a segment of a large or small intestine, umbilical artery or vein, ureter, mesenteric vessel and jugular vein.

In a preferred embodiment of the invention, the seamless tubular structures comprise a decellularized segment of fetal small intestine, i.e. small intestine derived from an adolescent mammal, such as a piglet.

In some embodiments of the invention, the seamless tubular structures and/or graft structures include at least one additional biologically active agent or composition, i.e. an agent that induces or modulates a physiological or biological process, or cellular activity, e.g., induces proliferation, and/or growth and/or regeneration of tissue.

In some embodiments, the biologically active agent comprises a cell, such as a human embryonic stem cell, cardiac stem cell, fetal cardiomyocyte, myofibroblast, mesenchymal stem cell, etc.

In some embodiments, the biologically active agent comprises a growth factor, such as a transforming growth factor-alpha (TGF-α), transforming growth factor-beta (TGF-β), fibroblast growth factor-2 (FGF-2), basic fibroblast growth factor (bFGF), and vascular epithelial growth factor (VEGF).

In some embodiments, the seamless tubular structures and/or graft structures include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor, such as cerivastatin.

In some embodiments of the invention, the seamless tubular structures and/or graft structures include at least one outer coating.

In some embodiments, the outer coating comprises a biodegradable polymeric composition coating.

In some embodiments of the invention, the seamless tubular structures and/or graft structures further comprise reinforcement means, i.e. reinforced vascular grafts.

In some embodiments, the reinforcement means comprises a thin strand or thread of reinforcing material that is wound around the tubular graft.

In some embodiments, the reinforcing strand comprises a biocompatible and biodegradable polymeric material.

In some embodiments, the reinforcing strand comprises an ECM strand or thread.

In some embodiments, the reinforcing strand comprises a biocompatible metal, such as stainless steel or Nitinol®, or a biocompatible and biodegradable metal, such as magnesium.

In some embodiments, the reinforcement means comprises a braided or mesh configuration.

In some embodiments of the invention, the seamless tubular structures and/or graft structures further comprise at least one anchoring mechanism.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
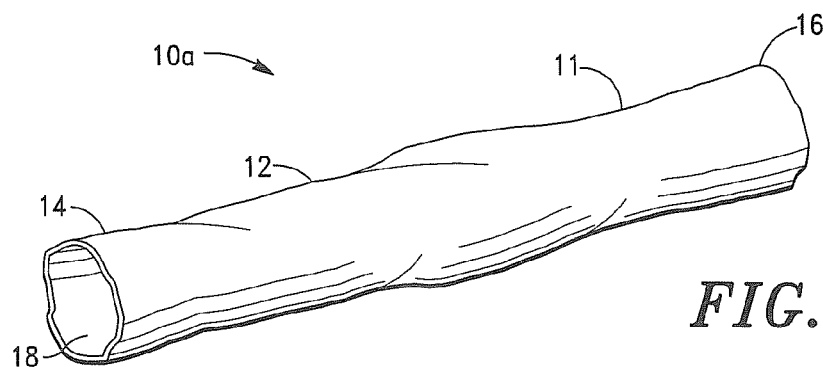
FIG. 1A is a perspective view of one embodiment of a seamless tubular structure, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a," "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The term "fetal", as used herein, means and includes an adolescent mammal, e.g., a piglet, preferably, less than three (3) years of age.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), liver basement membrane (LBM), intact basement membrane, central nervous system tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The term "mesothelial tissue", as used herein, means and includes epithelium of mesodermal origin. As is well known in the art, mesothelial tissue includes many of the seminal components, e.g., GAGs, growth factors, etc, that are contained in ECM.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuception, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor-alpha (TGF-α), transforming growth factor-beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor-alpha (TNA-α), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dennatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V anti-arrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofiupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to non-antigenic, resilient, bioremodelable, biocompatible tissue prostheses that can be engineered into a variety of shapes and used to repair, augment, reconstruct or replace damaged or diseased biological structures and associated tissue, including a pericardium, myocardium, heart valve, an aorta, artery, vein and vena cava, and other biological structures, including, without limitation, an esophagus, trachea, bronchus, ureter, urethra, bile duct, and small and large intestine. The tissue prostheses can also be readily employed to reconstruct or replace damaged or diseased dura around a spinal cord.

In a preferred embodiment of the invention, the tissue prostheses comprise seamless tubular members or conduits and graft structures.

As discussed in detail herein, in a preferred embodiment, the seamless tubular members (or conduits) comprise seamless tubular structures having first (or proximal) and second (or distal) ends.

It is to be understood that, although the invention is described in connection with seamless tubular structures, the description, e.g., compositions, applications, etc., are equally applicable to graft structures of the invention.

According to the invention, the seamless tubular structures of the invention can comprise any mammalian tubular structure, including, without limitation, a segment of a large or small intestine, umbilical artery or vein, ureter, mesenteric vessel and jugular vein.

In some embodiments, the seamless tubular structures of the invention thus comprise a segment of mammalian small intestine.

In a preferred embodiment, the seamless tubular member(s) of the invention comprises a segment of fetal or newborn small intestine. As indicated above, fetal small intestine means that the small intestine is derived from an adolescent mammal, such as a piglet, which is preferably less than three (3) years of age.

In a preferred embodiment, the seamless tubular structures are decellularized and, hence, remodelable. According to the invention, the seamless tubular structures can be decellularized by various conventional means.

In a preferred embodiment, the seamless tubular structures are decellularized via one of the unique Novasterilis processes disclosed in U.S. Pat. No. 7,108,832 and U.S. patent application Ser. No. 13/480,204; which are incorporated by reference herein in their entirety.

As set forth in U.S. application Ser. No. 13/480,204, additional biologically active and pharmacological agents can be disposed on and/or incorporated (or diffused) into the seamless tubular structures (and graft structures) of the invention.

According to the invention, upon implanting a seamless tubular structure (and/or graft structure) of the invention proximate a damaged tissue of a biological structure, the seamless tubular structure (and/or graft structure) induces "modulated healing."

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the seamless tubular structures and/or graft structures are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments of the invention, "modulated healing" means and includes the ability of a seamless tubular structure and/or graft structure to restrict the expression of inflammatory components. By way of example, according to the invention, when a seamless tubular structure and/or graft structure includes a coating comprising a statin augmented ECM composition, i.e. a composition comprising an ECM and a statin, and the seamless tubular structure or graft structure is disposed proximate damaged biological tissue, the seamless tubular structure and/or graft structure restricts expression of monocyte chemoattractant protein-1 (MCP-1) and chemokine (C—C) motif ligand 2 (CCR2).

In some embodiments, "modulated healing" means and includes the ability of a seamless tubular structure and/or graft structure to alter a substantial inflammatory phase (e.g., platelet or fibrin deposition) at the beginning of the tissue healing process. As used herein, the phrase "alter a substantial inflammatory phase" refers to the ability of a seamless tubular structure or graft structure to substantially reduce the inflammatory response at an injury site when in contact with biological tissue.

In such an instance, a minor amount of inflammation may ensue in response to tissue injury, but this level of inflammation response, e.g., platelet and/or fibrin deposition, is substantially reduced when compared to inflammation that takes place in the absence of a seamless tubular structure or graft structure of the invention.

The term "modulated healing" also refers to the ability of a seamless tubular structure or graft structure to induce host tissue proliferation, bioremodeling, including neovascularization, e.g., vasculogenesis, angiogenesis, and intussusception, and regeneration of tissue structures with site-specific structural and functional properties.

Thus, in some embodiments, the term "modulated healing" means and includes the ability of a seamless tubular structure and/or graft structure to modulate inflammation and/or induce host tissue proliferation and remodeling. Again, by way of example, according to the invention, when a seamless tubular structure or graft structure includes a coating comprising a statin augmented ECM composition, i.e. a composition comprising an ECM and a statin, and the seamless tubular structure or graft structure is disposed proximate damaged biological tissue, the seamless tubular structure and/or graft structure modulates inflammation by, among other actions, restricting expression of monocyte chemoattractant protein-1 (MCP-1) and chemokine (C—C) motif ligand 2 (CCR2) and induces tissue proliferation, bioremodeling and regeneration of tissue structures with site-specific structural and functional properties.

In some embodiments, when a seamless tubular structure or graft structure is in contact with damaged or diseased biological tissue, modulated healing is effectuated through the structural features of the seamless tubular structure or graft structure. The structural features provide the spatial temporal and mechanical cues to modulate cell polarity and alignment. The structural features further modulate cell proliferation, migration and differentiation thus modulating the healing process.

As stated above, in some embodiments of the invention, the seamless tubular structures (and/or graft structures) of the invention include at least one exogenously added biologically active agent or composition, i.e. an agent that induces or modulates a physiological or biological process, or cellular activity, e.g., induces proliferation, and/or growth and/or regeneration of tissue.

In a preferred embodiment of the invention, the biologically active agent is similarly derived from an adolescent mammal; preferably, a mammal less than three (3) years of age.

Suitable biologically active agents include any of the aforementioned biologically active agents, including, without limitation, the aforementioned cells and proteins.

In some embodiments of the invention, the biologically active agent comprises a growth factor selected from the group comprising transforming growth factor-alpha (TGF-α), transforming growth factor-beta (TGF-β), fibroblast growth factor-2 (FGF-2), basic fibroblast growth factor (bFGF) and vascular epithelial growth factor (VEGF).

According to the invention, upon implanting a seamless tubular structure and/or graft structure of the invention proximate damaged tissue of a biological structure, the exogenously added growth factor(s) links to and interacts with at least one molecule in the seamless tubular structure and/or graft structure, and further induces modulated healing, including enhanced modulation of inflammation, host tissue proliferation, bioremodeling, and regeneration of new tissue structures.

In some embodiments of the invention, the biologically active agent comprises a protein selected from the group comprising proteoglycans, glycosaminoglycans (GAGS), glycoproteins, heparins, chondroitin sulfate B (dermatan sulfate), chondroitin sulfate A, heparin sulfates, and hyaluronic acids.

In some embodiments of the invention, the protein comprises a cytokine selected from the group comprising a stem cell factor (SCF), stromal cell-derived factor-1 (SDF-1), granulocyte macrophage colony-stimulating factor (GM-CSF), interferon gamma (IFN-gamma), interleukin-3, interleukin-4, interleukin-10, interleukin-13, leukemia inhibitory factor (LIF), amphiregulin, thrombospondin 1, thrombospondin 2, thrombospondin 3, thrombospondin 4, thrombospondin 5, and angiotensin converting enzyme (ACE).

According to the invention, upon implanting a seamless tubular structure and/or graft structure of the invention in a cardiovascular system of a subject, the exogenously added protein(s) similarly links to and interacts with at least one molecule in the seamless tubular structure and/or graft structure and similarly further induces modulated healing, including enhanced modulation of inflammation, host tissue proliferation, bioremodeling, and regeneration of new tissue structures.

In some embodiments, the seamless tubular structures (and/or graft structures) of the invention include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, antineoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises one of the aforementioned anti-inflammatories.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

In some embodiments of the invention, the seamless tubular structures (and/or graft structures) of the invention include at least one outer coating.

In some embodiments, the outer coating comprises a biodegradable polymeric composition coating. According to the invention, suitable biodegradable polymeric compositions comprise, without limitation, formulations comprising polyurethane derivatives, polyhydroxyalkonates (PHAs), polylactides (PLLA) and polyglycolides (PLGA) and their copolymers, for example, poly(ε-caprolactone-co-glycolide), polyanhydrides, and like polymers.

Suitable polymeric composition coating formulations thus include formulations comprising poly-beta-hydroxybutyrate, poly(3-hydroybutyrate-co-3-hydroxyvalerate) (PHBV), Poly(3-hydroxybutyrate) (PHB), Poly(3-hydroxybutyrate-co-4-hydroxybutyrate) (P3HB4HB), Poly(3-hydroxybutyrate-co-3-hydroxyhexanoate) (PHBHHx), and Poly(3-hydroxyoctanoate-co-3-hydroxyhexanoate) (PHoHHx).

In some embodiments of the invention, the biodegradable polymeric composition coating comprises an ECM-mimicking biomaterial composition. In some embodiments, the ECM-mimicking biomaterial composition comprises poly (glycerol sebacate) (PGS).

As discussed in detail below, PGS exhibits numerous beneficial biochemical actions or activities. The properties and beneficial actions resulting therefrom are discussed in detail below.

PGS Physical Properties

PGS is a condensate of the non-immunogenic compositions glycerol (a simple sugar alcohol) and sebacic acid (a naturally occurring dicarboxylic acid), wherein, glycerol and sebacic acid are readily metabolized when proximate mammalian tissue. The non-immunogenic properties substantially limit the acute inflammatory responses typically associated with other "biocompatible" polymers, such as ePTFE (polytetrafluoroethylene), that are detrimental to bioremodeling and tissue regeneration.

The mechanical properties of PGS are substantially similar to that of biological tissue. Indeed, the value of the Young's modulus of PGS is between that of a ligament (in KPa range) and tendon (in GPa range). The strain to failure of PGS is also similar to that of arteries and veins (i.e. over 260% elongation).

The tensile strength of the PGS is at least $0.28\pm0.004$ MPa. The Young's modulus and elongation are at least $0.122\pm0.0003$ and at least $237.8\pm0.64\%$, respectively. For applications requiring stronger mechanical properties and a slower biodegradation rate, PGS can be blended with poly (ε-caprolactone) PCL, i.e. a biodegradable elastomer.

ECM Mimicking Properties/Actions

It has also been established that PGS induces tissue remodeling and regeneration when administered proximate to damaged tissue, thus, mimicking the seminal regenerative properties of ECM and, hence, an ECM composition formed therefrom. The mechanism underlying this behavior is deemed to be based on the mechanical and biodegradation kinetics of the PGS. See Sant, et al., *Effect of Biodegradation and de novo Matrix Synthesis on the Mechanical Properties of VIC-seeded PGS-PCL scaffolds*, Acta. Biomater., vol. 9(4), pp. 5963-73 (2013).

In some embodiments of the invention, the ECM-mimicking biomaterial composition further comprises one of the aforementioned ECM materials.

In some embodiments of the invention, the ECM-mimicking biomaterial composition comprises PGS and poly(ε-caprolactone) (PCL). According to the invention, the addition of PCL to the ECM-mimicking biomaterial composition enhances the structural integrity and modulates the degradation of the composition.

In some embodiments, the ECM-mimicking biomaterial composition comprises poly(glycerol sebacate) acrylate (PGSA), which, according to the invention, can be crosslinked and/or cured via the combination of a photoinitiator and radiation.

According to the invention, suitable photoinitiators for radiation induced crosslinking comprise, without limitation, 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl, methylcyclopentadienyl manganese tricarbonyl and any organometallatic photoinitiator that produces free radicals or cations.

According to the invention, suitable radiation wavelengths for crosslinking and/or curing the ECM-mimicking biomaterial composition comprise, without limitation, visible light; particularly, radiation in the range of approximately 380-750 nm, and ultraviolet (UV) light, particularly, radiation in the range of 10-400 nm, which includes extreme UV (10-121 nm), vacuum UV (10-200 nm), hydrogen lyman α-UV (121-122 nm), Far UV (122-200 nm), Middle UV (200-300 nm), Near UV (300-400 nm), UV-C (100-280 nm), UV-B (280-315 nm) and UV-A (315-400 nm) species of UV light.

In some embodiments, the ECM-mimicking biomaterial composition comprises a co-polymer of PGSA and polyethylene glycol (PEG) diacrylate.

Preferably, the ratio of PGSA to PEG diacrylate used when developing the photocured PGSA is proportional to the physical strength of the biomaterial composition, wherein a ratio of PGSA to PEG diacrylate in the range of 95:05-50:50 comprises a Young's modulus in the range of approximately 0.5-20 MPa respectively.

According to the invention, the Young's modulus will vary based on the configuration of the multi-laminate structure.

In some embodiments of the invention, the outer coating comprises an ECM composition comprising at least one of the aforementioned ECM materials.

In some embodiments of the invention, the outer coating comprises at least one of the aforementioned biologically active or pharmacological agents.

In some embodiments, the seamless tubular structures and/or graft structures comprise a combination of outer coatings having varying biologically active and/or pharmacological agents and/or properties, e.g. a first coating comprising a growth factor and a second coating comprising pharmacological agent.

In some embodiments, the outer coating(s) comprises modulated degradation kinetics, wherein the gradual degradation of the coating provides a controlled release of biologically active and/or pharmacological agents.

In some embodiments, the outer coating(s) is configured to provide a delivery gradient of various biologically active and/or pharmacological agent delivery profiles. By way of example, in some embodiments, biologically active and/or pharmacological agents are disposed throughout various depths or thickness ranges of the coating.

In some embodiments, wherein a seamless tubular structure and/or graft structure includes a plurality of outer coatings, the plurality of coatings is configured to provide a plurality of biologically active and/or pharmacological agent delivery profiles. By way of example, in some embodiments, a seamless tubular member can comprise a first coating comprising a growth factor augmented ECM composition, and a second coating comprising an ECM composition comprising a pharmacological agent, such as an anti-inflammatory or antiviral.

According to the invention, the outer coating can be applied to the seamless tubular structures and graft structures by any conventional means, including, without limitation, spray, dip coating, vapor deposition, etc.

In some embodiments of the invention, the seamless tubular structures further comprise reinforcement means, i.e. reinforced tubular members.

As discussed in detail below, in some embodiments, the reinforcement means comprises a thin strand or thread of reinforcing material that is wound around the tubular member. According to the invention, the reinforcing strand can comprise various biocompatible materials.

In a preferred embodiment, the reinforcing strand comprises a biocompatible and biodegradable polymeric composition. According to the invention, suitable biodegradable polymeric compositions can comprise compositions that include at least one of the aforementioned polymeric materials including, without limitation, polyhydroxyalkonates (PHAs), polylactides (PLLA) and polyglycolides (PLGA) and their copolymers, polyanhydrides, and like polymers.

A further suitable polymeric material comprises "Artelon", i.e. a poly(capralactone urea) material distributed by Artimplant AB in Goteborg, Sweden.

The polymeric composition can further comprise PGS and/or one of the aforementioned ECM-mimicking biomaterial compositions.

According to the invention, the reinforcing strand can also comprise an ECM strand or thread, such as a small intestine or urinary bladder submucosa suture.

According to the invention, the reinforcing strand can be disposed on the outer surface of the graft manually or via an electro-spin procedure.

According to the invention, the reinforcing strand can also comprise a biocompatible metal, such as stainless steel or Nitinol®, or a biocompatible and biodegradable metal, such as magnesium.

In some embodiments, the reinforcement means comprises a braided or mesh configuration or other conventional stent structure.

In some embodiments of the invention, the seamless tubular structures and/or graft structures further comprise at least one anchoring mechanism, such as disclosed in Co-pending application Ser. Nos. 13/782,024 and 13/686,131; which are incorporated by reference herein in their entirety.

Figure 1B:
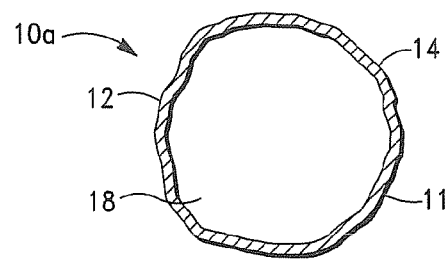
FIG. 1B is a side or edge plan view of the seamless tubular structure shown in FIG. 1A, in accordance with the invention.

Referring now to FIGS. 1A and 1B, there is shown one embodiment of a seamless tubular structure of the invention. As illustrated in FIG. 1A, the graft 10a comprises a continuous, seamless tubular conduit 12 having proximal 14 and distal 16 ends, and a lumen 18 that extends therethrough.

In a preferred embodiment of the invention, the seamless tubular conduit 12 comprises a decellularized segment of fetal small intestine.

According to the invention, the tubular conduit 12, and, hence seamless tubular structure 10a (and tubular structures 10b-10d, discussed below) formed therefrom, can be harvested from an adolescent mammal, e.g. fetal pig or piglet, at various lengths to accommodate specific applications.

According to the invention, the tubular conduit 12, and, hence seamless tubular a (and tubular members 10b-10d, discussed below) formed therefrom can have various diameters, e.g. 1.0 mm-5.0 cm.

In some embodiments of the invention, the seamless tubular structure 10a (or decellularized fetal small intestine tubular member 12) includes at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, growth factors and proteins.

In some embodiments, the seamless tubular structure 10a (or decellularized fetal small intestine tubular member 12) includes at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor.

Figure 2A:
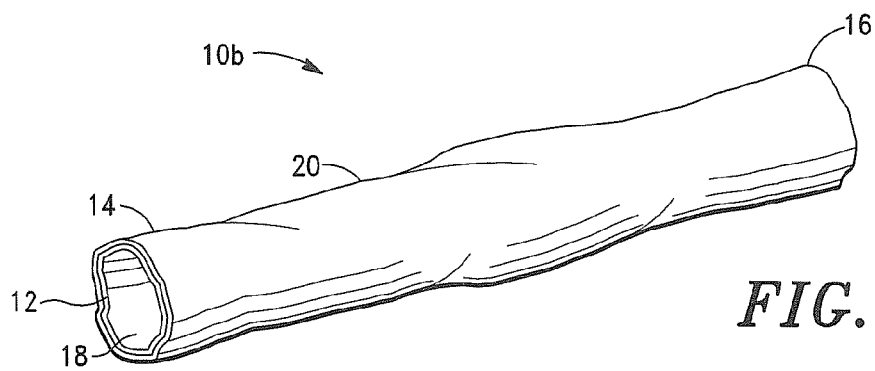
FIG. 2A is a perspective view of one embodiment of a coated seamless tubular structure, in accordance with the invention.
Figure 2B:
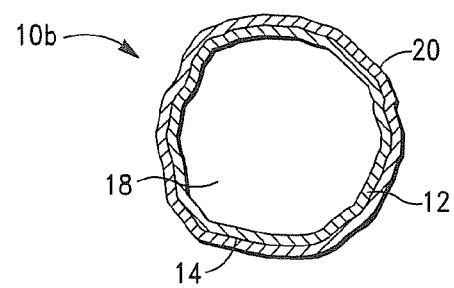
FIG. 2B is a side or edge plan view of the coated tubular structure shown in FIG. 2A, in accordance with the invention.

Referring now to FIGS. 2A and 2B, there is shown another embodiment of a seamless tubular structure of the invention. As illustrated in FIG. 2A, the seamless tubular structure 10b similarly comprises a continuous, seamless tubular conduit 12 having proximal 14 and distal 16 ends, and a lumen 18 that extends therethrough.

However, in this embodiment, the seamless tubular structure 10b further comprises at least one outer coating 20. In some embodiments, the outer coating 20 comprises one of the aforementioned outer coatings.

In some embodiments, the outer coating 20 comprises a pharmacological composition.

In some embodiments, the outer coating 20 comprises a biodegradable polymeric composition. As indicated above, suitable biodegradable polymeric compositions comprise, without limitation, formulations comprising polyurethane derivatives, polyhydroxyalkonates (PHAs). polylactides (PLLA) and polyglycolides (PLGA) and their copolymers, for example, poly(ε-caprolactone-co-glycolide), polyanhydrides, and like polymers.

In some embodiments of the invention, the biodegradable polymeric composition comprises an ECM-mimicking biomaterial composition. In some embodiments, the ECM-mimicking biomaterial composition comprises poly(glycerol sebacate) (PGS) a biodegradable polymeric coating.

As indicated above, in some embodiments of the invention, the seamless tubular structures of the invention further comprise reinforcement means, i.e. reinforced vascular grafts.

Figure 3A:
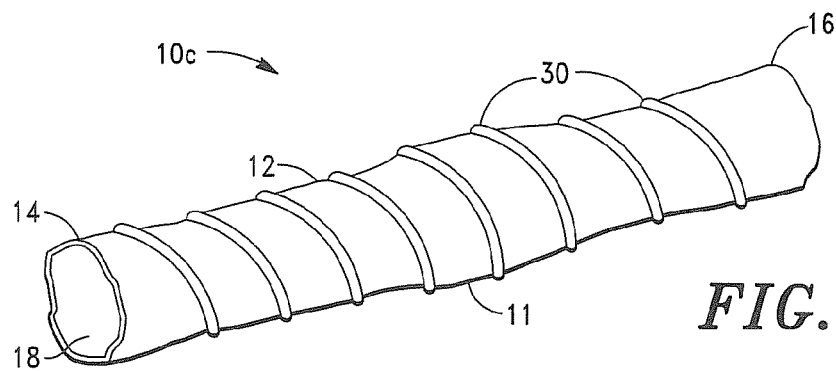
FIG. 3A is a perspective view of one embodiment of a reinforced seamless tubular structure, in accordance with the invention.
Figure 3B:
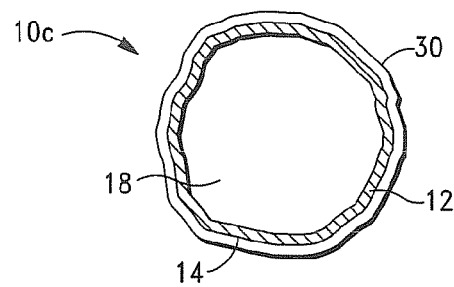
FIG. 3B is a side or edge plan view of the tubular structure shown in FIG. 3A, in accordance with the invention.

Referring now to FIGS. 3A and 3B there is shown one embodiment of a reinforced seamless tubular structure of the invention. As illustrated in FIG. 3A, the seamless tubular structure 10c similarly comprises a continuous, seamless tubular conduit 12 having proximal 14 and distal 16 ends, and a lumen 18 that extends therethrough.

The seamless tubular structure 10c further comprises reinforcement means, which, in the illustrated embodiment, comprises a thin strand or thread of reinforcing material 30, which is wound around the tubular graft 10c, and, hence, disposed proximate the outer surface 11 thereof. According to the invention, the reinforcing strand 30 can comprise various biocompatible materials.

As indicated above, in a preferred embodiment, the reinforcing strand 30 comprises a biocompatible and biodegradable polymeric material. Suitable biodegradable polymeric materials similarly include, without limitation, PGS, polyhydroxyalkonates (PHAs), polylactides (PLLA) and polyglycolides (PLGA) and their copolymers, polyanhydrides, and like polymers.

In some embodiments, the reinforcing strand 30 can alternatively comprise an ECM strand or thread, such as a small intestine or urinary bladder submucosa suture. In a preferred embodiment, the ECM strand comprises a cross-linked ECM material.

According to the invention, the reinforcing strand 30 can also comprise a biocompatible metal, such as stainless steel or Nitinol®, or a biocompatible and biodegradable metal, such as magnesium.

As indicated above, in some embodiments, the reinforcement means comprises a braided or mesh configuration.

Figure 4A:
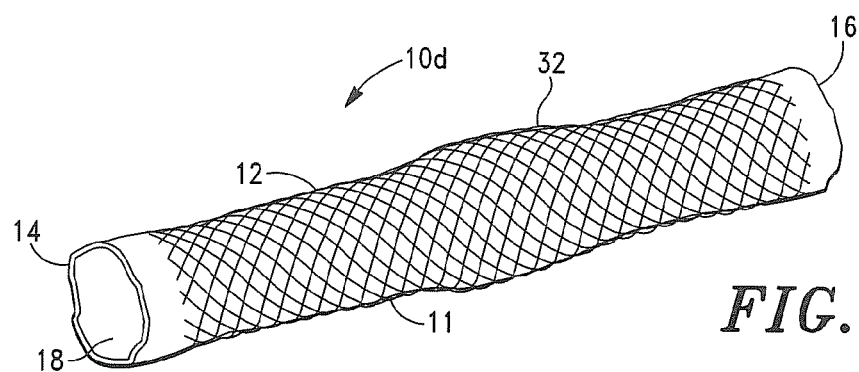
FIG. 4A is a perspective view of another embodiment of a reinforced seamless tubular structure, in accordance with the invention.
Figure 4B:
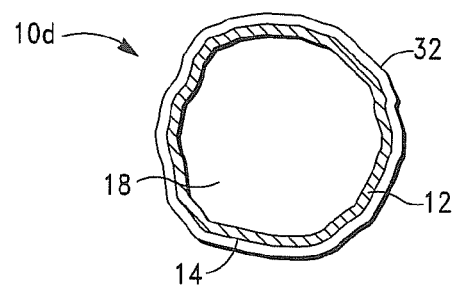
FIG. 4B is a side or edge plan view of the tubular structure shown in FIG. 4A, in accordance with the invention.

Referring now to FIGS. 4A and 4B there is shown another embodiment of a reinforced seamless tubular structure of the invention (denoted "10*d*"), wherein the tubular structure 10*d* includes a braided reinforcing structure 32.

According to the invention, the braided structure 32 can comprise various configurations and can be formed by various conventional means. The braided structure 32 can also comprise any of the aforementioned biocompatible and biodegradable materials.

In a preferred embodiment, the braided structure 32 comprises one of the aforementioned biodegradable polymeric materials.

In some embodiments, the seamless tubular structures 10*a*-10*c*1 further comprise at least one anchoring mechanism, such as disclosed in Co-pending application Ser. Nos. 13/782,024 and 13/686,131.

As will readily be appreciated by one having ordinary skill in the art, the present invention provides numerous advantages compared to prior art tissue prostheses. Among the advantages are the following:

- The provision of non-antigenic, resilient, bioremodelable, biocompatible tissue prostheses that can be engineered into a variety of shapes and used to repair, augment, reconstruct or replace damaged or diseased biological structures and associated tissue, including a pericardium, myocardium, heart valve, an aorta, artery, vein and vena cava, and other biological structures, including, without limitation, an esophagus, trachea, bronchus, ureter, urethra, bile duct, and small and large intestine.
- The provision of tissue prostheses, i.e. seamless tubular structures and graft structures, that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.
- The provision of tissue prostheses that can effectively replace or improve biological functions or promote the growth of new tissue in a subject.
- The provision of tissue prostheses that induce "modulated healing", including host tissue proliferation, bioremodeling and regeneration of new tissue and tissue structures with site-specific structural and functional properties.
- The provision of tissue prostheses that are capable of administering biologically active and pharmacological agents to host tissue and, thereby produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for reconstructing and replacing damaged biological structures and tissue, comprising the steps of:
   providing a tissue prosthesis comprising a seamless tubular member, said seamless tubular member comprising a decellularized mammalian tubular structure, said tubular structure having a first length, proximal and distal ends, an outer surface and a lumen that extends therethrough,
   said mammalian tubular structure further comprising at least one coating, said coating comprising poly(glycerol sebacate) (PGS), said PGS coating being disposed on at least a portion of said tubular structure outer surface,
   said coated mammalian tubular structure being configured to induce modulated healing when said tubular member is disposed proximate damaged biological tissue of a biological structure, said modulated healing comprising modulation of inflammation of said damaged tissue, host tissue proliferation, bioremodeling of said damaged tissue, and regeneration of new tissue and tissue structures with site-specific structural and functional properties; and
   disposing said tissue prosthesis proximate said damaged biological tissue of said biological structure, wherein said tubular member induces modulated healing of said damaged biological tissue and biological structure.

2. The method of claim 1, wherein said mammalian tubular structure comprises a segment of a mammalian structure selected from the group consisting of mammalian intestine, umbilical artery and vein, ureter, mesenteric vessel and jugular vein.

3. The method of claim 1, wherein said mammalian tubular structure comprises a segment of adolescent small intestine.

4. The method of claim 1, wherein said mammalian tubular structure further comprises at least a first exogenously added biologically active agent.

5. The method of claim 4, wherein said first biologically active agent comprises a growth factor selected from the group consisting of transforming growth factor-beta (TGF-β), and basic fibroblast growth factor (bFGF).

6. The method of claim 1, wherein said mammalian tubular structure further comprises a statin selected from the group consisting of atorvastatin, cerivastatin, fluvastatin, lovastatin, mevastatin, pitavastatin, pravastatin, rosuvastatin and simvastatin.

7. The method of claim 1, wherein said coating comprises an extracellular matrix (ECM) composition comprising an ECM material selected from the group consisting of small intestine submucosa (SIS), urinary bladder submucosa (UBS), stomach submucosa (SS), liver basement membrane (LBM), intact basement membrane, placental extracellular matrix, omentum extracellular matrix, cardiac extracellular matrix, kidney extracellular matrix, pancreas extracellular matrix, lung extracellular matrix, and combinations thereof.

8. The method of claim 1, wherein said mammalian tubular structure further comprises reinforcement means.

9. The method of claim 1, wherein said mammalian tubular structure further comprises at least one anchoring mechanism.

* * * * *